(12) United States Patent
Shimada et al.

(10) Patent No.: US 7,150,729 B2
(45) Date of Patent: Dec. 19, 2006

(54) DISPOSABLE PULL-ON WEARING ARTICLE

(75) Inventors: Takaaki Shimada, Kagawa-ken (JP); Naoko Takada, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 371 days.

(21) Appl. No.: 10/880,455

(22) Filed: Jul. 1, 2004

(65) Prior Publication Data

US 2005/0004545 A1   Jan. 6, 2005

(30) Foreign Application Priority Data

Jul. 2, 2003  (JP) .............................. 2003-190594

(51) Int. Cl.
*A61F 13/15* (2006.01)
*A61F 13/20* (2006.01)

(52) U.S. Cl. ............... 604/385.01; 604/365; 604/366; 604/367; 604/368; 604/385.25; 604/385.28; 604/385.24; 604/385.26; 604/385.27; 604/385.29; 604/385.3; 604/385.4; 604/385.101; 604/387

(58) Field of Classification Search ............... 604/365, 604/366, 367, 368, 385.01, 385.24–29, 385.101, 604/387

See application file for complete search history.

(56) References Cited

U.S. PATENT DOCUMENTS

| | | | |
|---|---|---|---|
| 6,323,387 B1 * | 11/2001 | Soga et al. | 604/368 |
| 6,638,262 B1 * | 10/2003 | Suzuki et al. | 604/385.28 |
| 6,710,222 B1 * | 3/2004 | Shimada et al. | 604/366 |
| 6,767,343 B1 * | 7/2004 | Shimada et al. | 604/385.25 |
| 2004/0133178 A1 | 7/2004 | Otsubo et al. | |
| 2005/0004548 A1 | 1/2005 | Otsubo et al. | |

FOREIGN PATENT DOCUMENTS

| | | |
|---|---|---|
| JP | 47-36734 | 12/1972 |
| JP | 50-33044 | 7/1973 |
| JP | 2003-10244 | 1/2003 |

* cited by examiner

*Primary Examiner*—Tatyana Zalukaeva
(74) *Attorney, Agent, or Firm*—Lowe Hauptman & Berner LLP

(57) ABSTRACT

A disposable pull-on wearing article wherein: a body fluid absorbent assembly of a disposable pull-on wearing article is formed in a crotch region with a pair of inwardly folded portions on both sides of a longitudinal center line. The body fluid absorbent assembly comprises an hourglass-shaped core and a cover sheet used to cover this core. The core is formed its both side edges with notches and respective regions of the cover sheet lying in these notches are provided with a pair of crotch region elastic members extending in a back-and-forth direction and intersecting folding guide lines.

4 Claims, 12 Drawing Sheets

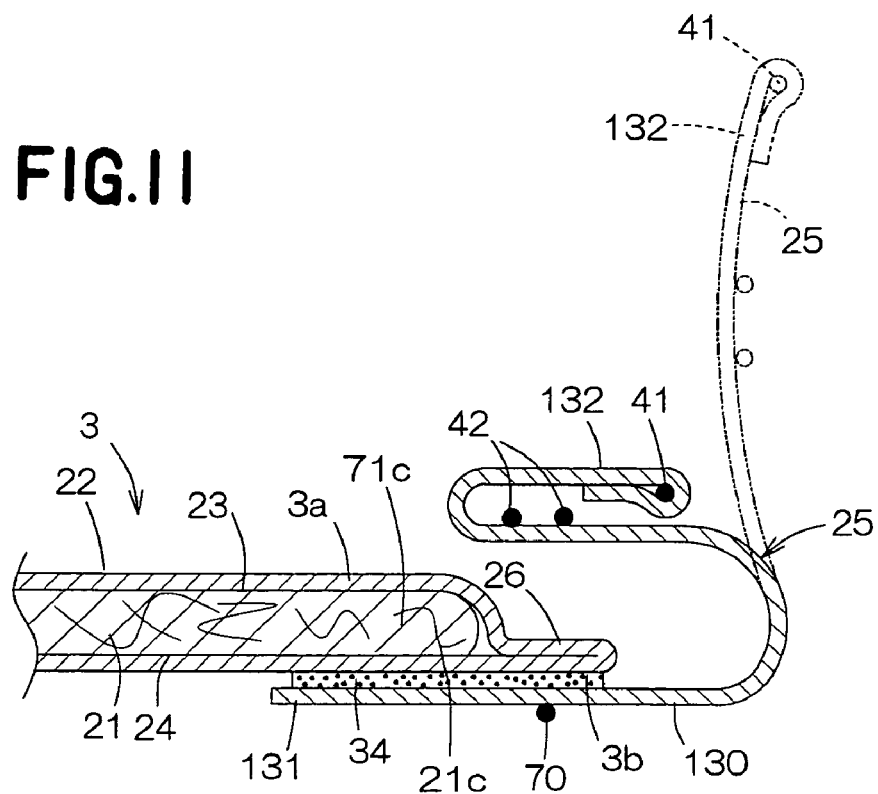
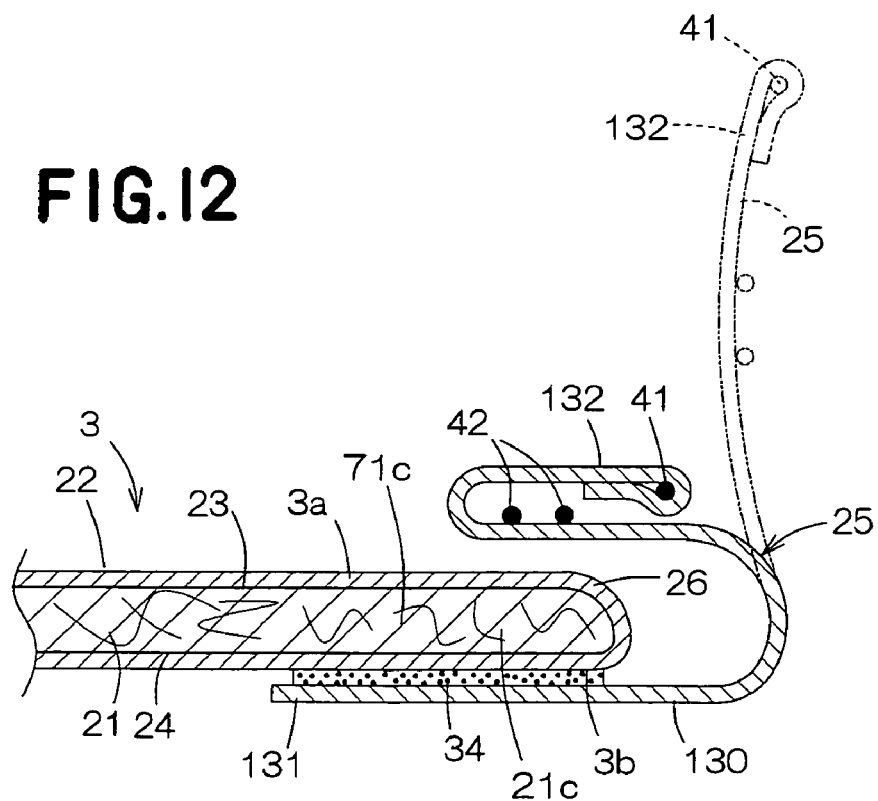

DISPOSABLE PULL-ON WEARING ARTICLE

RELATED APPLICATIONS

The present application is based on, and claims priority from, Japan Application Serial Number 2003-190594, filed Jul. 2, 2003, the disclosure of which is hereby incorporated by reference herein in its entirety.

BACKGROUND OF THE INVENTION

The present invention relates to disposable pull-on wearing articles such as disposable diapers, training pants, adult pants for incontinence or the like.

In disposable wearing articles such as disposable diapers including a rectangular body fluid absorbent panel, it is known to fold transversely opposite sectors of the panel inwardly of the panel in a crotch region of the diaper thereby to form a pair of folded portions.

For example, in a diaper disclosed in Japanese Unexamined Utility Model Application Publication No. 1972-36734 (Citation 1), a rectangular panel-like chassis has folded portions in the crotch region and each of these folded portions is symmetrically formed about a crossline bisecting a longitudinal dimension of the chassis. In other words, each of the folded portions is formed so as to be symmetric in a back-and-forth direction of the diaper.

The diaper disclosed in Japanese Unexamined Patent Application Publication No. 1975-33044 (Citation 2) also is formed with the folded portions. These folded portions are formed by folding the rectangular body fluid absorbent panel-like material along the transverse center line and the lines radially extending from the midpoint of this transverse center line so that the inner surface of the diaper which are opposed to itself in these folded portions may be partially bonded together. The folded portions in this diaper also are symmetric about the transverse center line, in other words, as viewed in the back-and-forth direction of the diaper.

The pull-on wearing article disclosed in Japanese Unexamined Patent Application Publication No. 2003-10244 (Citation 3) is adapted to be used in the form of disposable pull-on diaper or the like and includes the rectangular body fluid absorbent panel normally curved in a U-shape and extending over the crotch region and further into the front and rear waist regions. This panel also is provided in the crotch region with a pair of folded portions formed by folding the panel along the panel crossing line extending across the bottom of the pants-type wearing article and the lines radially extending from the midpoint of the crossing line to the transversely opposite side edges of the panel. In this wearing article also, each of these folded portions is symmetrically formed about the crossing line, in other words, symmetrically formed as viewed in the back-and-forth direction of the wearing article.

In every wearing article disclosed in Citations 1, 2 and 3, the folded portions of the panel in the crotch region function to locally reduce the width of the panel and, at the same time, function as the pockets adapted to contain bodily discharges.

It is common to the disclosures of Citations 1, 2 and 3 that the folded portions of the body fluid absorbent panel are symmetric as viewed in the back-and-forth direction of the diaper and the body fluid absorbent panel after formation of these folded portions is also substantially symmetric as viewed in the back-and-forth direction of the diaper. The panels are destined to cover the wearer's back side with the rear zone of the panel extending behind the folded portions and to cover the wearer's belly side with the front zone of the panel extending in front of the folded portions. However, if the panel is dimensioned to be sufficiently wide to cover the wearer's hip with the rear zone of the panel in leak-free fashion, the front zone of such wide panel will obstruct free movement of the wearer's legs. On the other hand, if the panel is dimensioned to be sufficiently narrow to avoid the anxiety that the front zone of the panel might obstruct free movement of the wearer's legs, the absorbing capacity of the panel in the vicinity of the wearer's hip will be insufficient to avoid leak of body fluids.

SUMMARY OF THE INVENTION

In view of the problem as has been described above, it is an object of the present invention to provide a disposable pull-on wearing article wherein a body fluid absorbent assembly has a pair of folded portions in a crotch region improved to be free from an anxiety that the body fluid absorbent assembly might obstruct movement of a diaper wearer's legs and might cause leak of body fluids.

According to the present invention, there is provided a disposable pull-on wearing article having a front waist region and a rear waist region, the crotch region being provided with a body fluid absorbent assembly extending over the crotch region and further into the front and rear waist regions, the body fluid absorbent assembly having transversely opposite side edges extending substantially in parallel to each other into the front and rear waist regions and longitudinally curving substantially in U-shape with its inner surface opposed to itself in the front and rear waist regions and, in the crotch region, the body fluid absorbent assembly has a pair of first folding guide lines extending from a midpoint of a crossline extending across the crotch region or from two points on the crossline which are equidistant in opposite directions from the midpoint to the transversely opposite side edges of the body fluid absorbent assembly placed aside toward the front waist region at a crossing angle a with respect to the crossline, a pair of second folding guide lines extending from the midpoint or the two points to the transversely opposite side edges of the body fluid absorbent assembly placed aside toward the rear waist region at a crossing angle $\beta$ with respect to the crossline, a pair of folded portions formed by folding inward respective sectors of the body fluid absorbent assembly defined between the first and second folding guide lines, a first non-folded portion extending aside from the pair of the first folding guide lines toward the front waist region and a second non-folded portion extending aside from the pair of the second folding guide lines toward the rear waist region.

The article further comprises the body fluid absorbent assembly comprising a body fluid absorbent core and a body fluid pervious cover sheet adapted to cover the core and to define at least the inner surface of the body fluid absorbent assembly, the core being formed on both sides of the crotch region with notches so as to have a relatively narrow width in the crotch region and a relatively large width in the front and rear waist regions and thereby to present an hourglass-like shape as a whole, the cover sheet having a width substantially in conformity with the sections of the core lying in the front and rear waist regions but having extending outward beyond the notches in the crotch region, and the extensions of the cover sheet beyond the notches or any sheet placed upon the extensions of the cover sheet being provided with crotch region elastic members attached thereto in stretched or non-stretched state so that the crotch region elastic members extend in the back-and-forth direction and intersect the first and second folding guide lines.

The present invention may include the following embodiments.

The body fluid absorbent assembly is provided along the opposed side edges with leak-barrier cuffs each made of a sheet member, the respective sheet members being folded back in the transverse direction of the body fluid absorbent assembly from the outer surface onto the outer surface so as to cover the opposite side edges and respective outer side edges of the sheet members lying on the outer surface being bonded to the outer surface, longitudinally opposite ends of the respective sheet members lying in the front and rear waist regions being bonded to the outer and inner surfaces, in the notches of the core, the respective sheet members lying on the outer surface being bonded to the cover sheet and the crotch region elastic members being bonded to respective the sheet members.

The crossing angles $\alpha$, $\beta$ are in a range of 10° to 60° and the crossing angle $\beta$ is in a range of 10 to 30°.

The pants-type wearing article is formed with a pair of leg-holes and a leg elastic members attached to upper halves of peripheral portions surrounding the respective leg-holes intersect the adjacent ends of the crotch region elastic members.

BRIEF DESCRIPTION OF THE DRAWINGS

FIG. 11 is a sectional view taken along the line XI—XI in FIG. 10;

FIG. 12 is a sectional view taken along the line XII—XII in FIG. 10.

DETAILED DESCRIPTION OF THE PREFERRED EMBODIMENTS

Details of a disposable pull-on wearing article according to the present invention will be more fully understood from the description of a pants-type diaper as a typical embodiment of the invention given hereunder with reference to the accompanying drawings.

Figure 1:
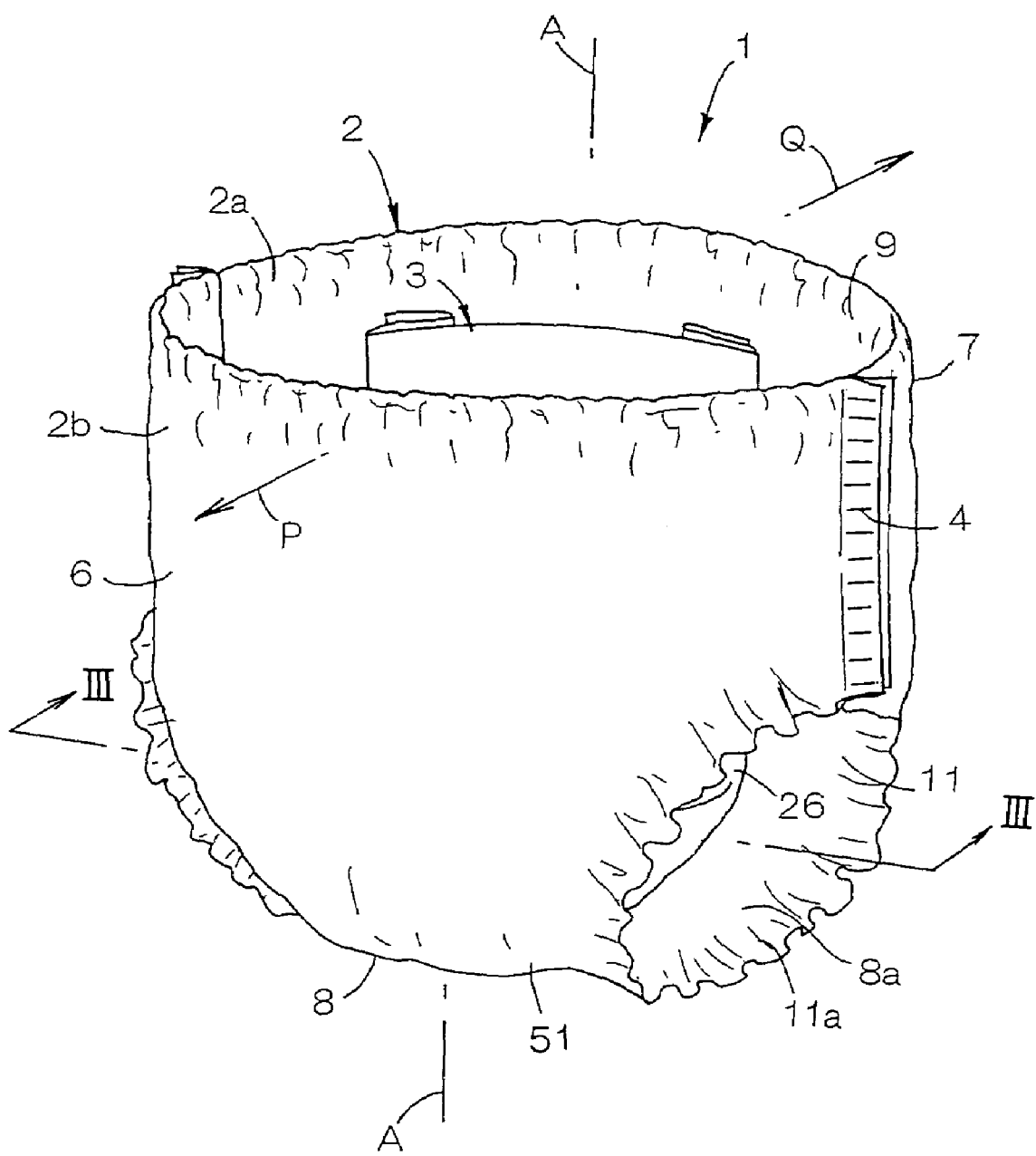
FIG. 1 is a perspective view showing a pull-on diaper as a typical embodiment of the invention.
Figure 2:
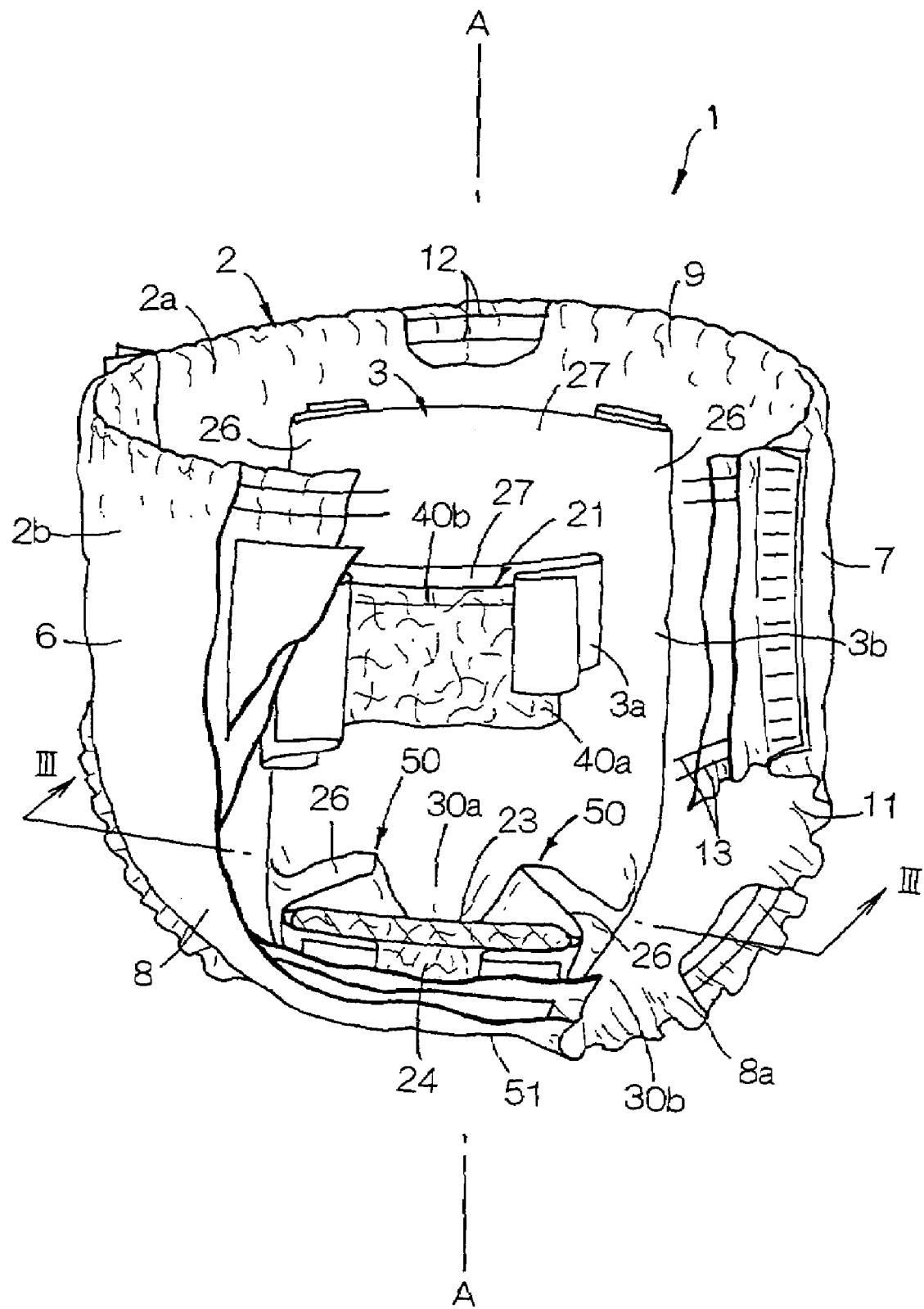
FIG. 2 is a partially cutaway perspective view showing the diaper of FIG. 1.
Figure 3:
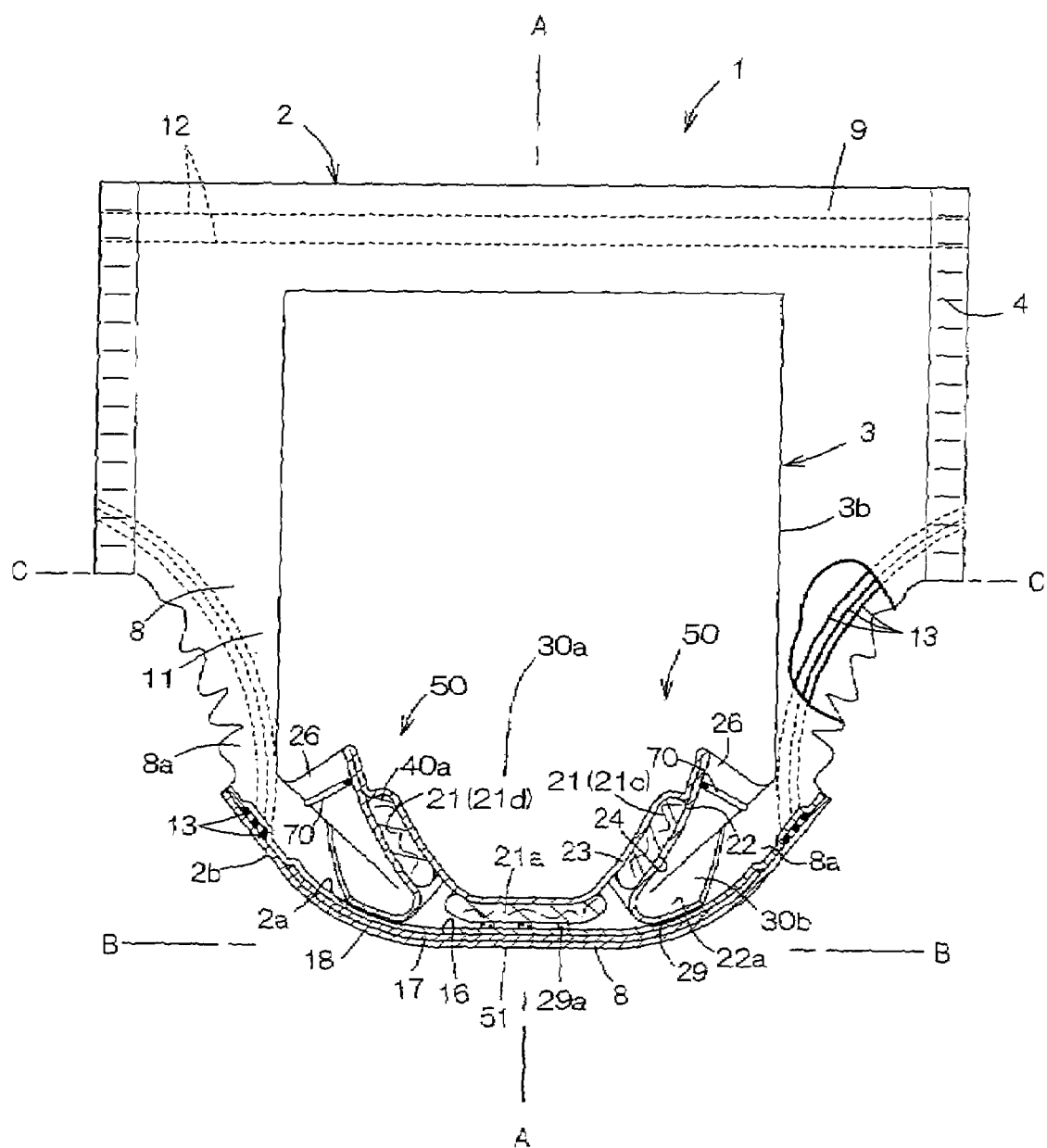
FIG. 3 is a sectional view taken along the line III—III in FIG. 1.

FIG. 1 is a partially cutaway perspective view showing a pull-on disposable diaper 1. FIG. 2 is a perspective view showing the diaper 1 of FIG. 1 and FIG. 3 is a sectional view taken along the line III—III in FIG. 1. A cross-section defined by the line III—III corresponds to a plane along which the diaper 1 of FIG. 1 is divided into a front waist region 6 and a rear waist region 7 and in which an internal structure of the bottom 51 of the diaper 1 appears. The diaper 1 has a height direction, a width direction and a back-and-forth direction which are orthogonal one to another. The height direction corresponds to a vertical direction in FIG. 1, the width direction corresponds to a direction extending along the line III—III in FIG. 1, in other words, a transverse direction in FIG. 3 and the back-and-forth direction corresponds to a direction indicated by arrows P and Q. The diaper 1 comprises a pull-on covering chassis 2 and a body fluid absorbent assembly 3 being capable of absorbing and containing bodily fluids discharged by a wearer. The covering chassis 2 has an inner surface 2a facing the diaper wearer's skin and an outer surface 2b facing the diaper wearer's clothes and defines the front and rear waist regions 6, 7 adapted to cover the front and rear waist regions of the diaper wearer, respectively, and a crotch region 8 adapted to cover a crotch region of the diaper wearer. The front and rear waist regions 6, 7 are put flat and bonded together in the vicinity of transversely opposite side edges of the diaper 1 at a plurality of spots 4 arranged intermittently in the vertical direction of the diaper 1 so that these waist regions 6, 7 may define a waist-hole 9 and these waist regions 6, 7 may cooperated with the crotch region 8 to define a pair of leg-holes 11. The waist-hole 9 and the leg-holes 11 are provided in the vicinity of peripheral edges thereof with a plurality of elastic members 12, 13, respectively, bonded thereto in stretched state. The body fluid absorbent assembly 3 lies on the inner surface 2a of the covering chassis 2 and extends over the crotch region 8 and further into the front and rear waist regions 6, 7 wherein the body fluid absorbent assembly 3 curves substantially in U-shape with its inner surface being mutually opposed to itself. The absorbent assembly 3 includes, in the vicinity of the bottom 51 of the diaper 1, a pair of folded portions 50 which are defined by transversely opposite side edges 26 partially folded inward as viewed in the width direction of the diaper 1 toward a longitudinal center line A—A (See FIG. 4 also) extending in the height direction (i.e., vertical direction as viewed in FIG. 1) so as to bisect the width of the diaper 1.

Figure 4:
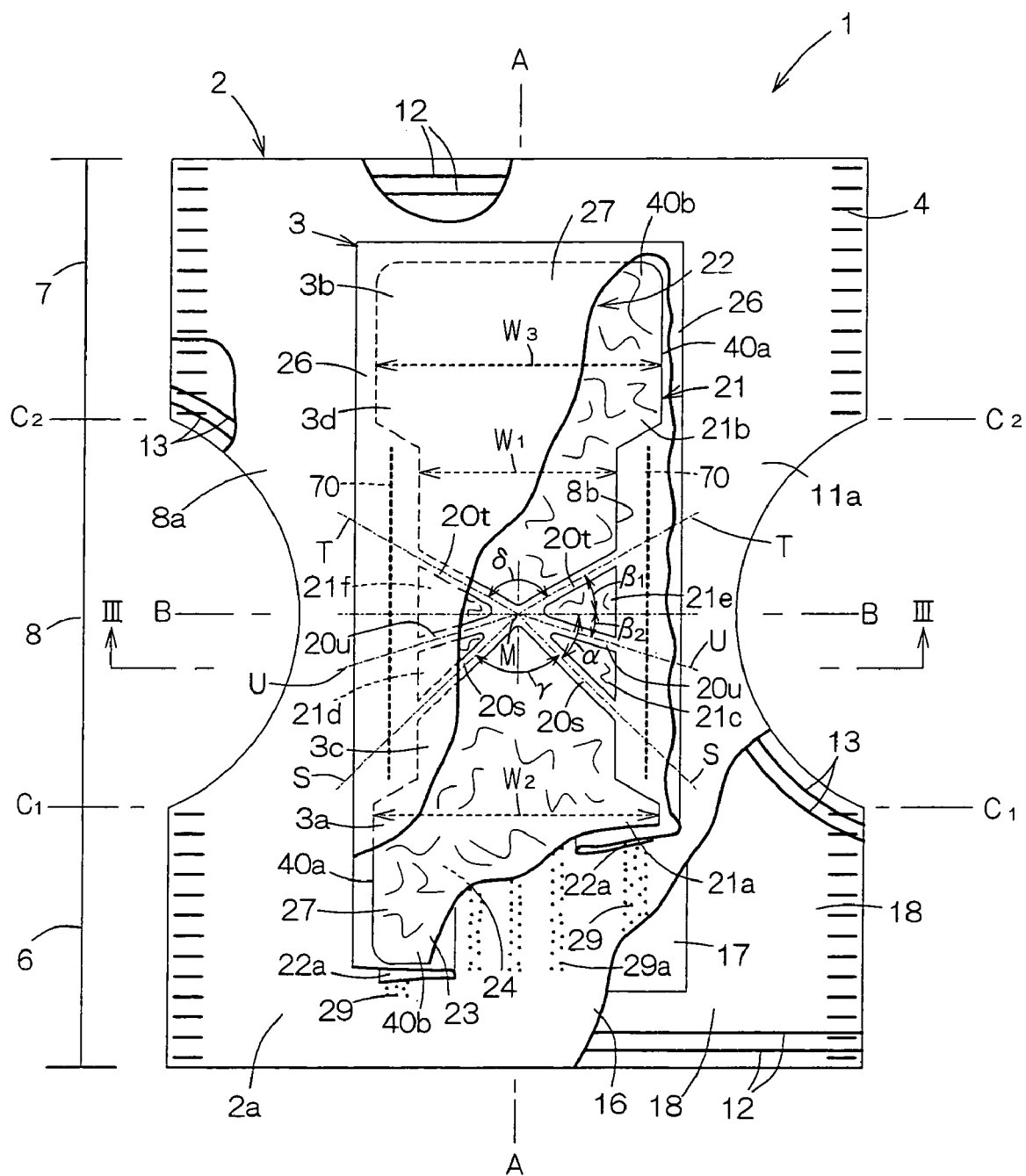
FIG. 4 is a plan view showing the diaper of FIG. 1 as has been developed.

FIG. 4 is a plan view showing the diaper 1 of FIG. 1 with the front and rear waist regions 6, 7 having been peeled off from each other at the bonded spots 4 and developed in the opposite directions indicated by the arrows P and Q as partially broken away. In FIG. 4 showing the diaper 1 developed in this manner, a crossline B—B is illustrated to extends across the diaper 1 so as to bisect a longitudinal dimension of the diaper 1 and to intersect with the longitudinal center line A—A at its midpoint M. With respect to the crossline B—B, the line III—III is placed aside toward the front waist region 6 and FIG. 3 is a sectional view taken along this lien III—III. The diaper 1 of FIG. 4 is substantially symmetric about the longitudinal center line A—A and folded inward along the crossline B—B to form the diaper 1 of FIG. 1, wherein the crossline B—B extends along the bottom 51 of the diaper 1 (See FIG. 3). The midpoint M of the longitudinal center line A—A coincides with a midpoint of the crossline B—B. Upper and lower lines $C_1$—$C_1$ and $C_2$—$C_2$ defining an extent of the crotch region 8 in FIG. 4 are superposed on each other to in the diaper 1 of FIG. 3 and define a single line C—C passing through crests of the respective leg-holes 11 in parallel to the crossline B—B.

The covering chassis 2 comprises, as illustrated by FIG. 4, an hourglass-shaped inner sheet 16 made of a breathable nonwoven fabric, more preferably made of a hydrophobic breathable nonwoven fabric, an intermediate sheet 17 made of a liquid-impervious plastic film, more preferably made of a breathable liquid-impervious plastic film presenting a rectangular shape of substantially the same size as a planar size of the absorbent assembly 3 or of a size larger than the planar size of the absorbent assembly 3 and lying on an outer surface of the inner sheet 16 and an outer sheet 18 made of a breathable nonwoven fabric and identical to the inner sheet 16 in size as well as in shape and lying on an outer surface of the intermediate sheet 17. These sheets 16, 17, 18 are laminated and intermittently bonded one to another by means of adhesive or suitable welding technique. The inner sheet 16 and the outer sheet 18 constituting the covering chassis 2 both made of a nonwoven fabric contribute to a soft touch of this covering chassis 2. The waist and leg elastic members 12, 13 interposed between these inner and outer sheets 16, 18 are bonded to at least one of these sheets 16, 18 by means of adhesive (not shown).

The absorbent assembly 3 comprises a body fluid absorbent core 21 and a body fluid pervious cover sheet 22 and has a substantially rectangular shape which is defined by the cover sheet 22 and vertically longer in FIG. 4. The absorbent assembly 3 has a pair of transversely opposite side edges 26 extending substantially parallel to the longitudinal center line A—A over the crotch region 8 and further into the front and rear waist regions 6, 7 and a pair of longitudinally opposite ends 27, 28 extending substantially parallel to the crossline B—B across the diaper 1 (See FIG. 2 also). A crotch section 8 of the absorbent assembly 3 and a crotch section 8 of the covering chassis 2 refer to the respective sections defined between a pair of parallel lines $C_1$—$C_1$ and $C_2$—$C_2$ in FIG. 4 and, referring to FIG. 3, these sections are defined between the crossline B—B and the line C—C.

The core 21 has an hourglass-like shape defined by sections lying in the front and rear waist regions 6, 7 and notches 8b formed therebetween. The core 21 has a width $W_1$ in the crotch region 8 and widths $W_2$, $W_3$ in the front and rear waist regions 6, 7, respectively. In the illustrated embodiment of the core 21, the width $W_2$ is substantially same as the width $W_3$ and one half of a difference between the width $W_2$ and the width $W_1$ corresponds to a dimension of the notch 8b as viewed in the transverse direction of the core 21. The core 21 has an inner surface 23 facing the diaper wearer's skin, an outer surface 24 facing the diaper wearer's garment, transversely opposite lateral surfaces 40a connecting the inner and outer surfaces 23, 24 and extending in the longitudinal direction, and longitudinally opposite ends 40b transversely extending in the front and rear waist regions 6, 7, respectively. The core 21 is destined to be folded along a pair of first folding guide lines S which extend from the midpoint M on the longitudinal center line A—A to the points on the side edges 26 lying aside toward the front waist region 6 substantially in a V-shape, a pair of second folding guide lines T which extend from the midpoint M to points on the side edges 26 lying aside toward the rear waist region 7 substantially in V-shape and a pair of third folding guide lines U which extend between those folding guide lines S and T from the midpoint M to points on the side edges 26 lying aside toward the front waist region 6 substantially in V-shape. To facilitate operation of folding, the core 21 further includes first, second and third folding guide grooves 20s, 20t and 20u extending along the respective folding guide lines S, T, U. These guide grooves 20s, 20t and 20u divide the core 21 into core elements 21a, 21b, 21c, 21d, 21e and 21f. The crossline B—B crosses the first folding guide lines S at an angle $\alpha$, the crossline B—B crosses the second guide lines T at an angle $\beta_1$ and the crossline B—B crosses the guide lines U at an angle $\beta_2$. A preferred angle $\alpha$ is in a range of 10° to 60° and a preferred angle $\beta_1$ is also in a range of 10° to 30°. As will be described in more detail with reference to FIG. 4, the angle $\beta_2$ is an angle automatically determined as the sections of the side edges 26 extending between the first and second guide grooves 20s, 20t are folded along these grooves 20s, 20t inward with respect to the absorbent assembly 3 as best seen in FIGS. 2 and 3.

In the absorbent assembly 3, each of the core elements 21a–21f is formed from compressing a water absorbent material such as fluff pulp and/or super-absorbent polymer particles under an appropriate pressure and, if desired, wrapping the core element compressed in this manner with water-absorbing and diffusing sheet such as a tissue paper or nonwoven fabric of thermoplastic synthetic fibers modified to be hydrophilic. The inner surfaces 23 of the core elements 21a–21f or a tissue paper or the like (not shown) covering these inner surfaces 23 may be bonded to the cover sheet 22. The outer surfaces 24 of the core elements 21a–21f or a tissue paper or the like covering these outer surfaces 24 may be bonded to the inner sheet 16 or the like by means of adhesive 29a. The cover sheet 22 transversely extends to cover the inner surface 23, the opposite lateral surfaces 40a and zones of the outer surface 24 contiguous to these lateral surfaces 40a. Below the outer surface 24, the transversely opposite side edges 22a of the cover sheet 22 are folded back outward in the transverse direction of the core 21 and bonded to the inner surface of the inner sheet 16 by means of hot melt adhesive 29. The cover sheet 22 or the portions of the core 21 extending outward beyond its longitudinally opposite end surfaces 40b are bonded to the inner sheet 16 by means of hot melt adhesive (not shown). Thus, the cover sheet 22 is folded in a Z-shape or an inverted Z-shape in the vicinity of the lateral surfaces 40a of the core 21 (See FIG. 3). Stock materials for the cover sheet 22 may be selected from the group including a liquid-pervious nonwoven fabric, a porous plastic film and a laminated sheet comprising these nonwoven fabric and film.

In the absorbent assembly 3 shown in FIGS. 3 and 4, crotch region elastic members 70 are attached in stretched or non-stretched state to the outer surface of the cover sheet 22 or the tissue paper (not shown) extending in the vicinity of the notches 8b of the absorbent assembly 3 by means of hot melt adhesive (not shown). As indicated by thick chain lines in FIG. 4, these crotch region elastic members 70 are orthogonal to the crossline B—B on both sides of the center line A—A so as to intersect the first, second and third folding guide lines S, T, U and rectilinearly extend on the crotch region 8a in the back-and-forth direction. Each of the crotch region elastic member 70 comprises a single elastic element or a plurality of elastic elements.

The diaper 1 having the absorbent assembly 3 formed as has been described above may be converted from the developed state as shown in FIG. 4 to the state as shown by FIG. 1 by folding the developed diaper 1 along the crossline B—B with the absorbent assembly 3 inside and bonding the front and rear waist regions 6, 7 together at the spots 4. In this course, portions of the absorbent assembly 3 lying in the crotch region 8 and divided by the longitudinal center line A—A in two are folded toward the longitudinal center line A—A, i.e., inwardly of the absorbent assembly 3, as shown by FIGS. 2 and 3. More specifically, the absorbent assembly 3 is folded inward along the first and second folding guide grooves 20s, 20t so that, in each of right and left halves of the absorbent assembly 3, the respective outer surfaces 24 of the core elements 21c, 21e are opposed to each other (See FIG. 4) and the respective outer surfaces 24 of the core elements 21d, 21f are opposed to each other while the inner surface 23 of the core element 21a is opposed to the respective inner surfaces 23 of the core elements 21c, 21d and the inner surface 23 is opposed to the respective inner surfaces 21e, 21f. In this way, the absorbent assembly 3 is formed with a pair of the folded portions 50. The rectangular absorbent assembly 3 having been curved in U-shape and folded inward along the first and second folding guide grooves 20s, 20t may be further flatly folded until the inner surface of the absorbent assembly 3 substantially comes in contact with itself to fold the core 21 along the third folding guide grooves 20u also, which are positioned so that the core elements 21c, 21e having already been folded may be placed upon each other and the core elements 21d, 21f may be placed upon each other. The first, second and third folding guide lines S, T, U of the absorbent assembly 3 folded in this manner may be the grooves 20s, 20t, 20u in which the core 21 is absent as in the illustrated embodiment or the grooves merely to guide folding. In either case, in the absorbent assembly 3 having been folded, the folded lines are formed more easily in the vicinity of the longitudinal center line A—A than in the vicinity of the notches 8b and the folded lines once formed easily disappear in the regions of the cover sheet 22 extending in the vicinity of the notches 8b due to elastic restoration of the crotch region elastic members 70 to their states before the cover sheet 22 is folded.

As will be apparent from FIGS. 2 and 3, the absorbent assembly 3 of the diaper 1 is formed between the respective folded portions 50 with a pocket 30. The pocket 30 maintains a sufficiently large upper opening to reliably receive even viscous body discharges such as loose passage since the regions of the cover sheet 22 extending in the vicinity of the notches 8b are substantially free from the folded lines under elastic restoration of the crotch region elastic members 70.

In the diaper 1 according to the invention, the absorbent assembly 3 is provided in the crotch region 8 and thereby the width of the crotch region 8 is appropriately reduced to improve a feeling to wear the diaper 1. The pocket 30 defined by the folded portions 50 has a sufficiently large upper opening to reliably receive body discharges flowing thereinto.

Figure 5:
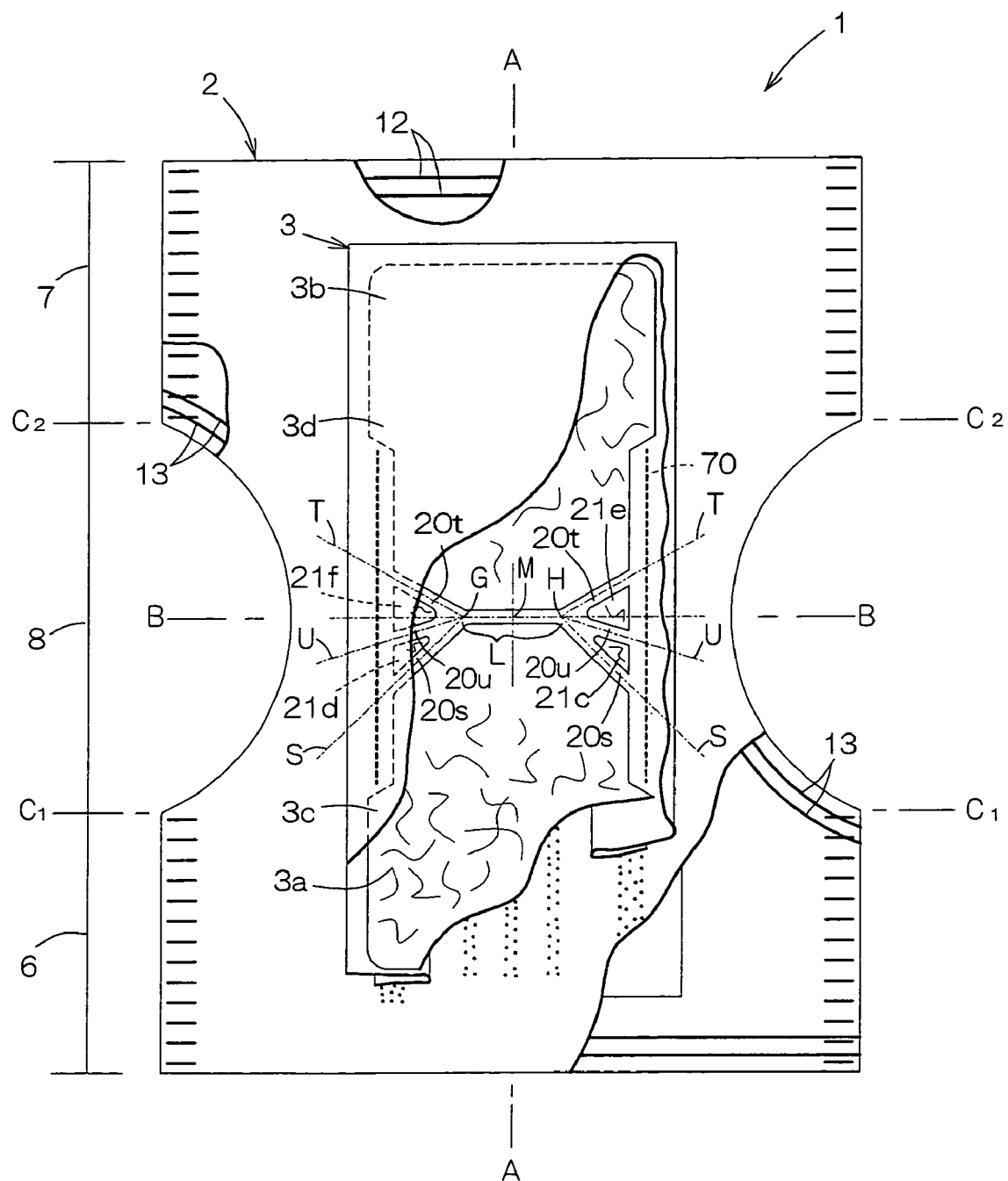
FIG. 5 is a view similar to FIG. 4, showing one preferred embodiment of the invention.

FIG. 5 is a view similar to FIG. 4, showing one preferred embodiment of the invention. In the absorbent assembly 3 of this diaper 1, the first, second and third folding guide lines S, T, U and the first, second and third folding guide grooves 20s, 20t, 20u corresponding to the folding guide lines S, T, U extend toward the opposite side edges 26 from two points G, H which lie on the crossline B—B and equidistant from the midpoint of the crossline B—B. Similarly to the case of the diaper 1 shown by FIG. 4, the absorbent assembly 3 is folded along the first, second and third folding guide grooves 20s, 20t, 20u to form the folded portions 50. In this diaper 1 also, the crotch region elastic members 70 are attached in stretched or non-stretched state to the outer surface of the cover sheet 22 in the vicinity of the notches 8b of the core 21.

The diaper 1 illustrated in FIGS. 1 through 5 may be altered so that the crotch region 8 in the covering chassis 2 has a width dimensioned to be same as or narrower than the width of the absorbent assembly 3 in its state illustrated by FIG. 4. In this case, the outer surface 24 of the core 21 may be covered with a liquid-impervious sheet which may be, in turn, bonded to the covering chassis 2. Such bonding may be achieved by bonding the absorbent assembly 3 to the front waist region 6 and to the rear waist region 7 but not to the crotch region 8. For the diaper 1 with the absorbent assembly 3 is bonded to the covering chassis 2 in this manner, the covering chassis 2 having the crotch region 8 cutaway, i.e., comprising the front waist region 6 and the rear waist region 7 may be used. While the invention has been described on the basis of the diaper 1 as the typical embodiment, the present invention is applicable to the other wearing articles such as training pants, incontinence pants and sanitary pants.

Figure 6:
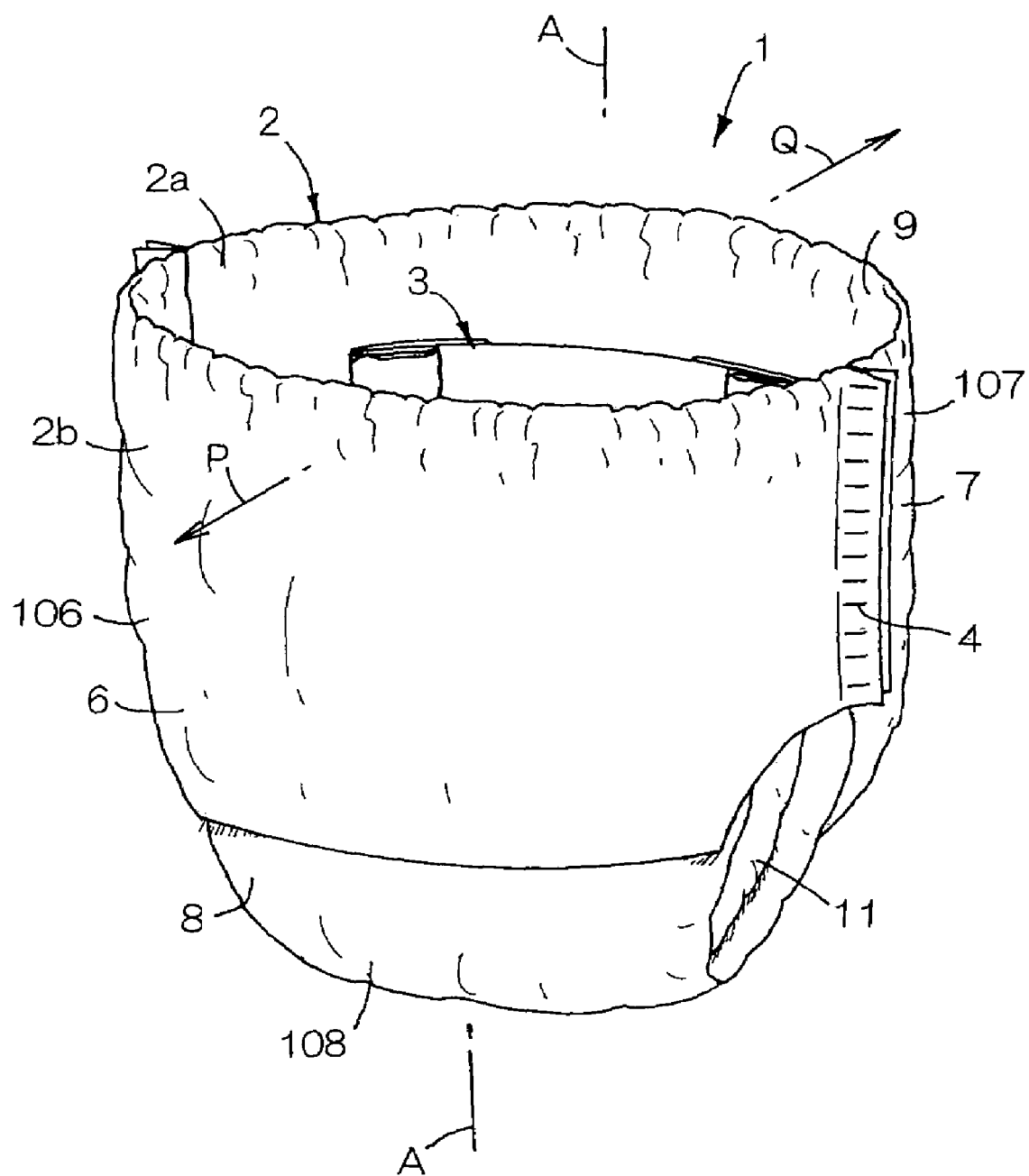
FIG. 6 is a view similar to FIG. 1, showing another preferred embodiment of the invention.
Figure 7:
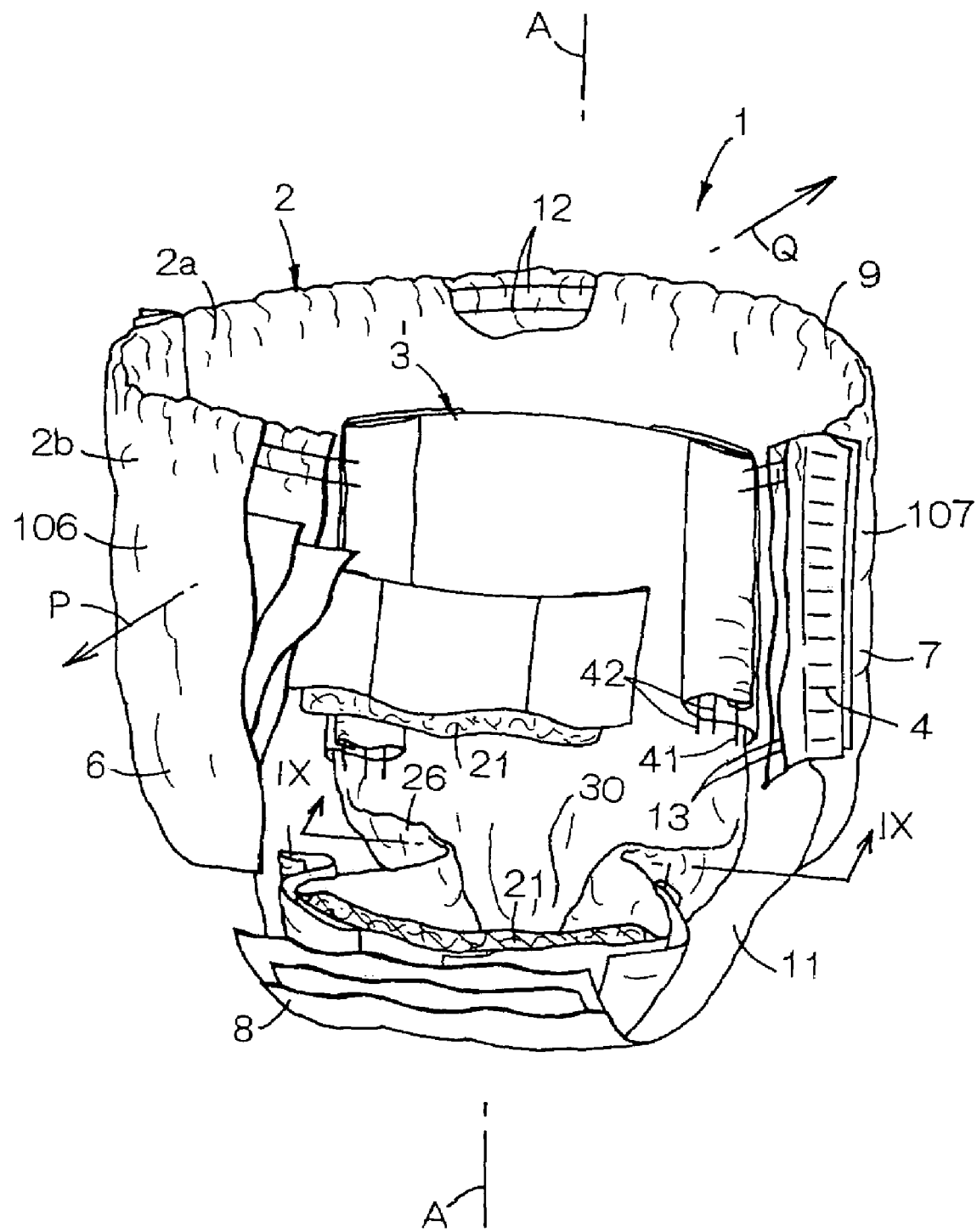
FIG. 7 is a partially cutaway perspective view showing the diaper of FIG. 6.

FIG. 6 is a view similar to FIG. 1, showing the diaper 1 as another preferred embodiment of the invention and FIG. 7 is a partially cutaway perspective view showing the diaper 1 of FIG. 6. Similarly to the case as has been described in reference with FIG. 1, this diaper 1 basically comprises the pants-type covering chassis 2 and the body fluid absorbent assembly 3 wherein a plurality of waist elastic members 12 are attached in stretched state to the peripheral portion of the waist-hole 9 of the covering chassis 2. For the leg-holes 11, a plurality of leg elastic members 13 are attached in stretched state to front and rear sheets 106, 107 which form the front and rear waist regions 6, 7, respectively, and define substantially upper halves of the peripheral portions of the respective leg-holes 11. In this way, the elastic members 13 for the respective leg-holes 11 describe substantially semi-circular curves. The absorbent assembly 3 lies on the inner surface 2a of the covering chassis 2 and extends over the crotch region 8 further into the front and rear waist regions 6, 7. In the crotch region 8, transversely opposite side edges of the absorbent assembly 3 are cut toward the longitudinal center line A—A, i.e., cut inward as viewed in the transverse direction of the diaper 1 so as to reduce a width of the absorbent assembly 3.

Figure 8:
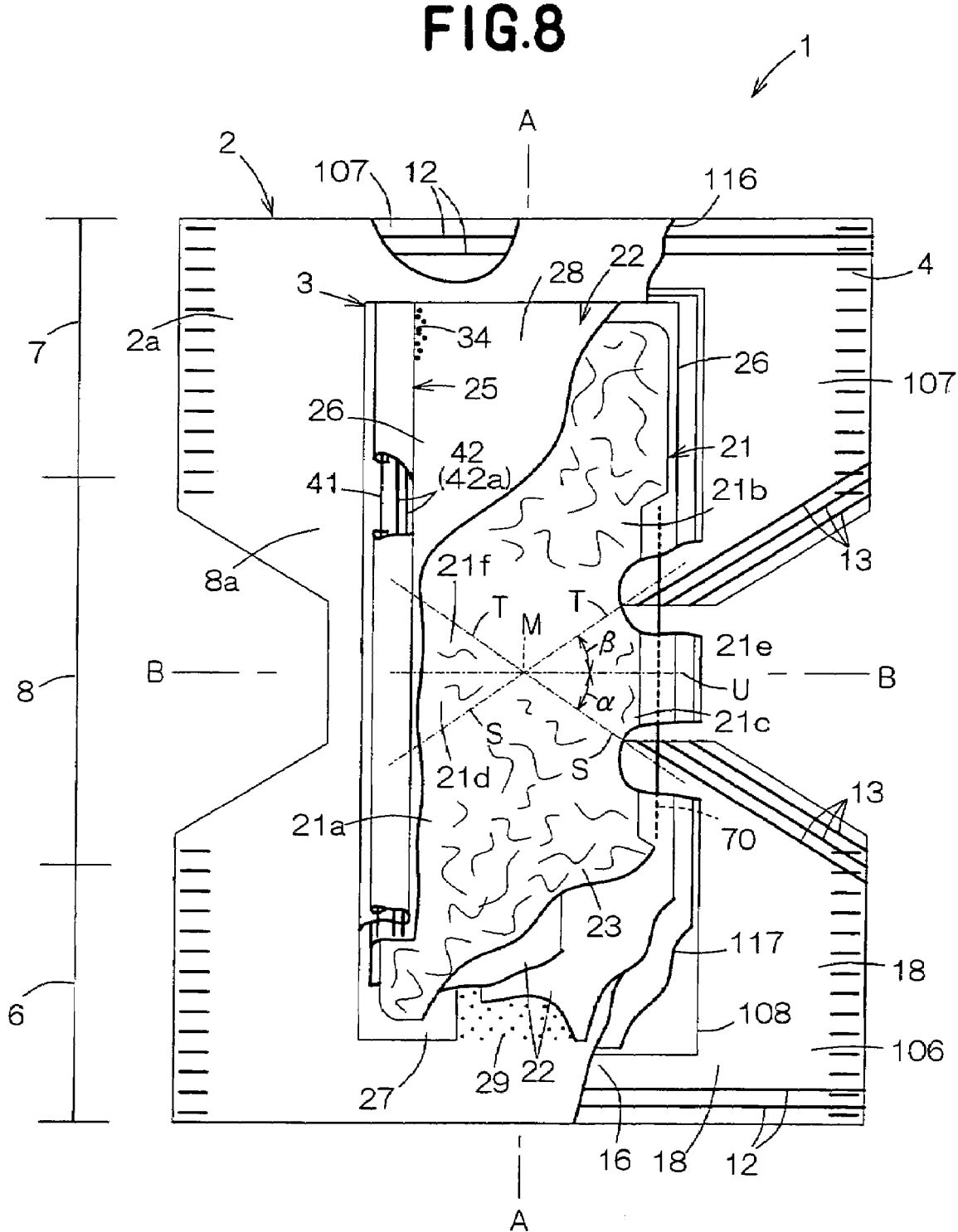
FIG. 8 is a plan view showing the diaper of FIG. 6 as has been developed.
Figure 9:
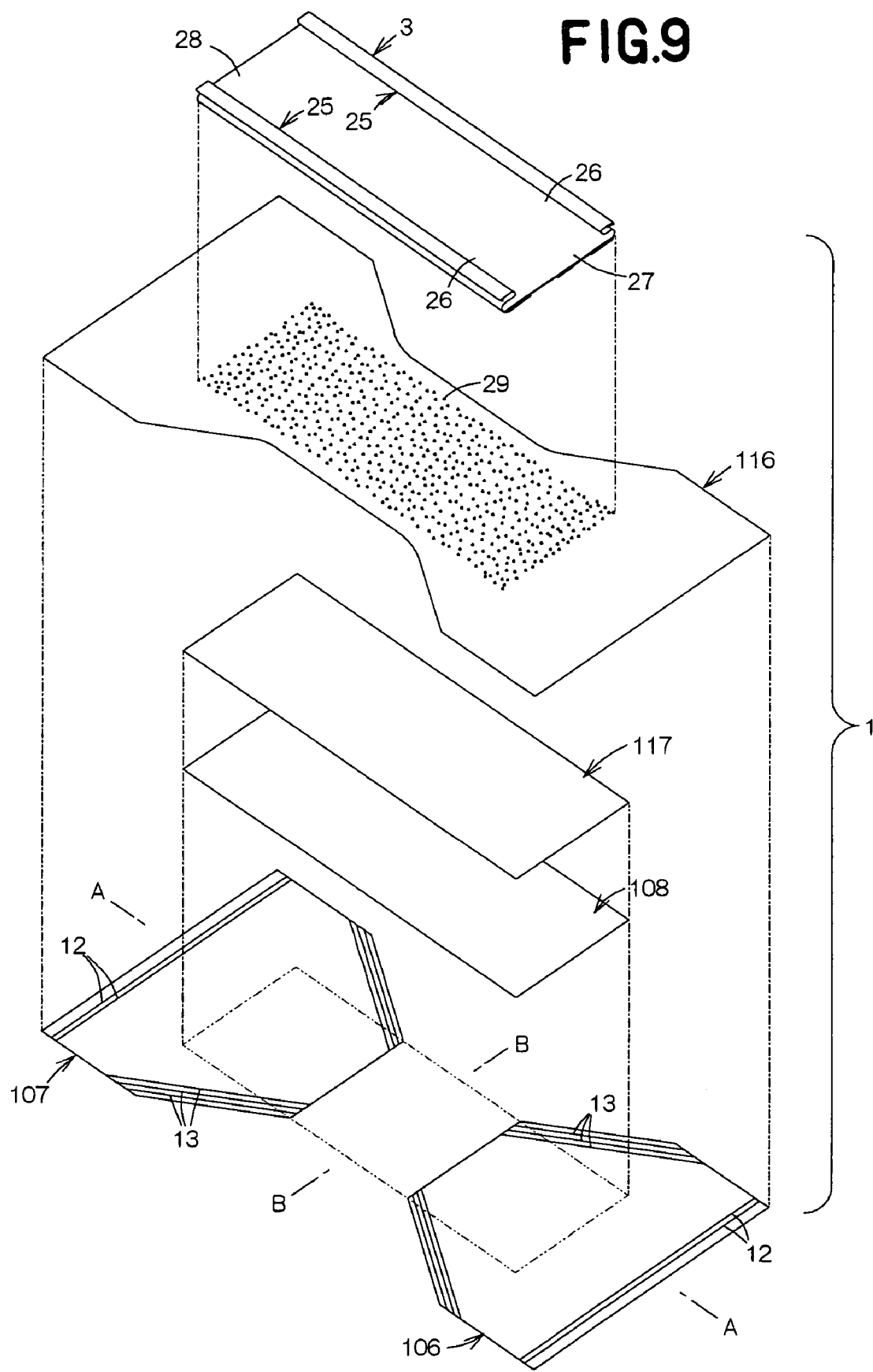
FIG. 9 is an exploded perspective view showing the diaper of FIG. 8.

FIG. 8 is a plan view showing the diaper of FIG. 6 with the front and rear waist regions 6, 7 having been separated one from another along arrays of the spots 4 and developed in the opposite directions indicated by the arrows P, Q in FIG. 6 as partially broken away and FIG. 9 is an exploded perspective view showing the diaper 1 of FIG. 8. In the diaper 1 developed in this manner, the transverse center line B—B is orthogonal to the longitudinal center line A—A and bisects a length of the developed diaper 1.

The covering chassis 2 comprises a hexagonal front sheet 106 defining the front waist region 6 and a part of the crotch region 8, a rear sheet 107 defining the rear waist region 7 and a part of the crotch region 8 and a rectangular center sheet 108 defining a part of the crotch region 8. The front and rear sheets 106, 107 are provided on their inner surfaces with the waist elastic members 12 and the leg elastic members 13 attached thereto. The center sheet 108 has its front and rear ends bonded to the inner surfaces (i.e., upper surfaces as viewed in FIG. 9) of the front and rear sheets 106, 107, respectively, by means of hot melt adhesive (not shown) so as to connect the front and rear sheets 106, 107 to each other. A rectangular intermediate sheet 117 made of liquid-impervious plastic film is placed upon the inner surface of the center sheet 108 and an hourglass-shaped inner sheet 116 is placed upon the inner surface of the intermediate sheet 117. The intermediate sheet 117 is substantially same as the center sheet 108 in the shape but slightly smaller than the center sheet 108. The inner sheet 116 is substantially same as an hourglass-shaped assembly of the front and rear sheets 106, 107 and the center sheet 108 in size as well as in shape. These sheets 106, 107, 108, 117 and 116 are intermittently bonded one to another in regions of these sheets overlapping one to another. The rectangular body fluid absorbent assembly 3 having its length in a direction defining a length of the center sheet 108 is bonded to the inner surface of the inner sheet 116. The absorbent assembly 3 has its substantially entire outer surface 24 intermittently bonded to the inner sheet 116 by means of hot melt adhesive 29 applied on the inner sheet 116.

The absorbent assembly 3 has a rectangular shape which is relatively long in vertical direction as viewed in FIG. 8 and this rectangular shape is contoured by a pair of transversely opposite side edges 26 extending in parallel to the longitudinal center line A—A and longitudinally opposite ends 27, 28 being orthogonal to the side edges 26 and extending in the transverse direction (i.e., width direction) of the diaper 1. The absorbent assembly 3 further includes the leak-barrier cuffs 25 extending along the respective side edges 26. Such absorbent assembly 3 comprises the body fluid absorbent core 21 and the body fluid pervious cover sheet 22. On both sides of the crotch region 8, the core 21 is formed with the notches 8b so that the core 21 has a relatively narrow width in the crotch region 8 and relatively large width in the front and rear waist regions 6, 7, thus presenting the hourglass-shape. The core 21 is destined to be folded together with the cover sheet 22 along a pair of the first folding guide lines S which extend from the midpoint M of the core 21 at which the longitudinal center line A—A intersects the transverse center line B—B to the side edges 26 substantially in V-shape, a pair of the second folding guide lines T which extend from the midpoint M to the side edges 26 substantially in V-shape and a third folding guide line U which coincides with the transverse center line B—B These folding guide lines S, T, U divide the core 21 into core elements 21a, 21b, 21c, 21d, 21e and 21f. The cover sheet 22 covers the inner and outer surfaces of the core 21 and has its transversely opposite ends overlapping at a transversely middle region of the outer surface so as to wrap the core 21. In the crotch region 8, the cover sheet 22 extends laterally beyond the side edges of the respective notches 8b of the core 21 and, along these extensions, the cover sheet 22 placed upon and bonded together preferably by means of hot melt adhesive (not shown).

Figure 10:
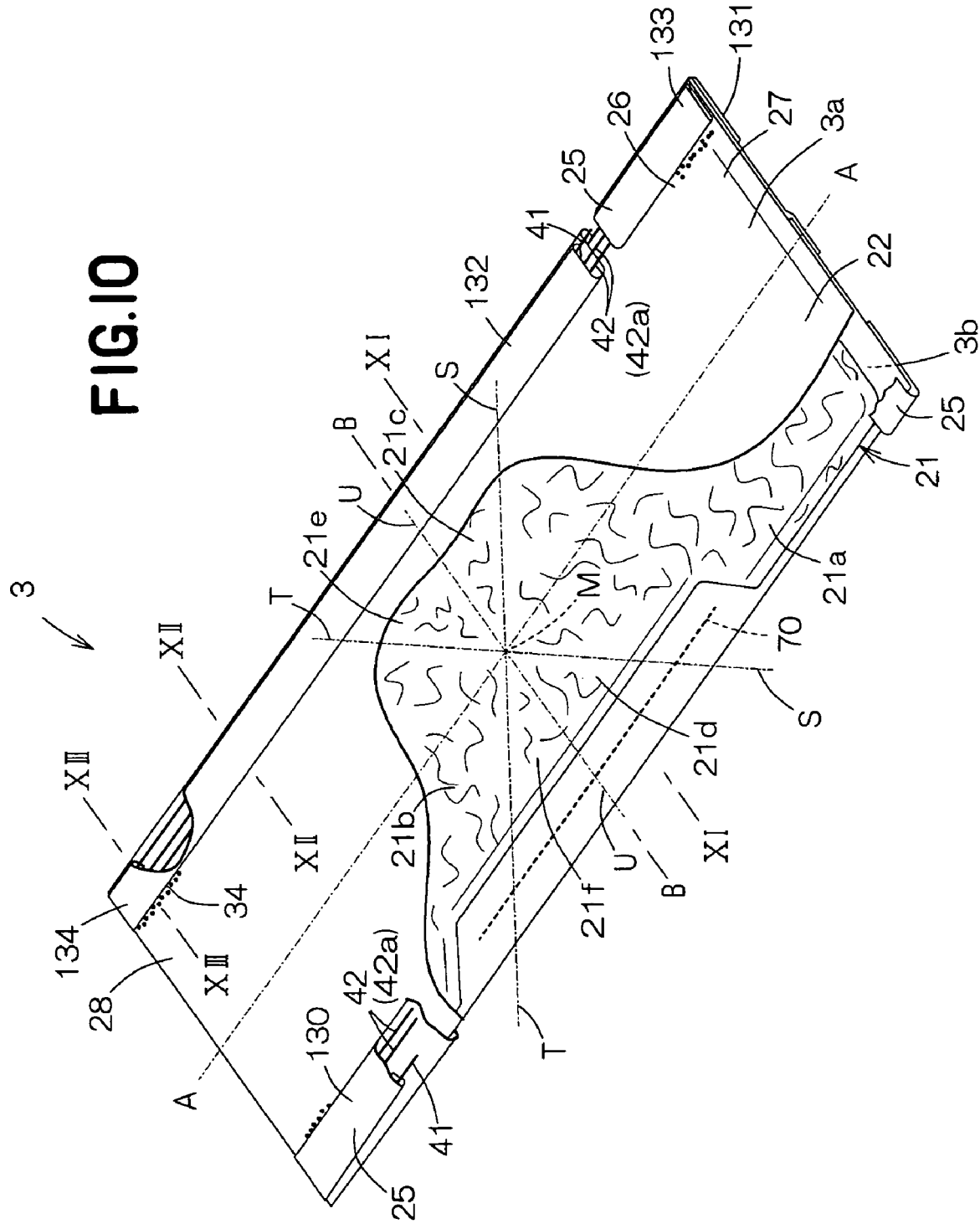
FIG. 10 is a partially cutaway perspective view showing an absorbent assembly in the diaper of FIG. 9.
Figure 13:
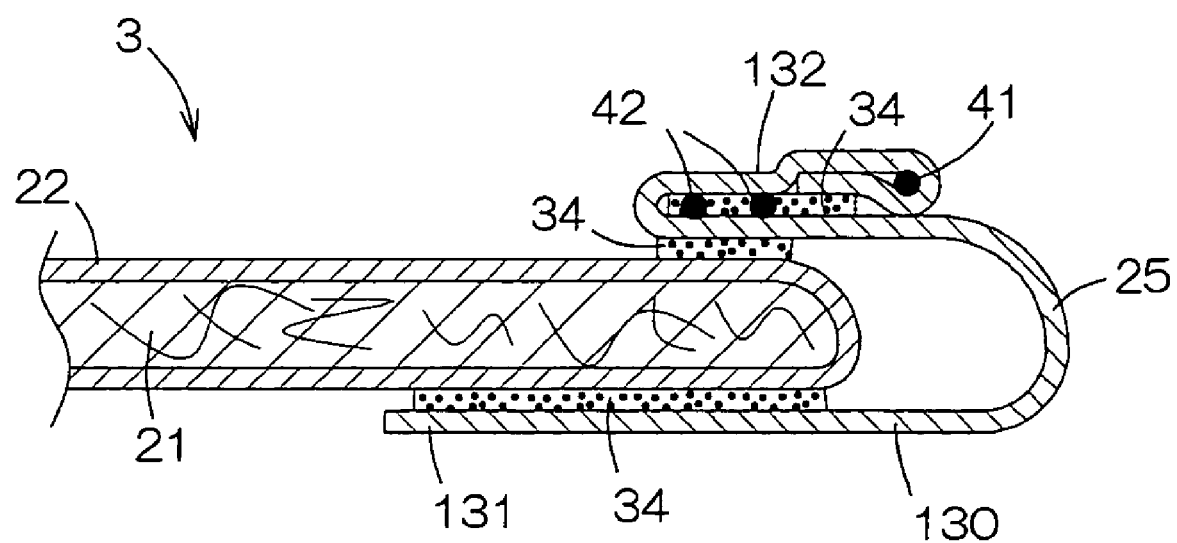
FIG. 13 is a sectional view taken along the line XIII—XIII in FIG. 10.

FIG. 10 is a partially cutaway perspective view showing the absorbent assembly and FIGS. 11, 12 and 13 are sectional views taken along lines XI—XI, XII—XII and XIII—XIII in FIG. 10, respectively. Each of the leak-barrier cuffs 25 is formed by a sheet member extending along each of the side edges 26 of the absorbent assembly 3 and, as this sheet member, a hydrophobic, preferably, hydrophobic and liquid-impervious, more preferably, hydrophobic, breathable and liquid-impervious nonwoven fabric or a plastic film is used. The leak-barrier cuff 25 is folded in the transverse direction of the absorbent assembly 3 in a Z-shape or an inverted Z-shape and has an outer side edge 131 lying below an outer surface 3b of the absorbent assembly 3 and an inner side edge 132 lying above an inner surface 3a of the absorbent assembly 3. The outer side edge 131 is bonded to the cover sheet 22 by means of adhesive 34. The outer side edge 131 is provided in its region lying along the notch 8b of the core 21 with the crotch region elastic member 70 comprising a single elastic element or a plurality of elastic elements attached thereto in stretched or non-stretched state by means of hot melt adhesive (not shown). The crotch region elastic member 70 extends in the back-and-forth direction in the absorbent assembly 3 over a range as exemplarily indicated by the thick chain lines in FIG. 8. The crotch region elastic member 70 can not be seen in both sectional views of FIGS. 12 and 13. The crotch region elastic member 70 in this embodiment is distinguished from the embodiment shown by FIGS. 4 and 5 in that, instead of being attached directly to the cover sheet 22 covering the core 21, the crotch region elastic member 70 is indirectly attached to the cover sheet 22 through the intermediary of the sheet member forming the leak-barrier cuff 25 with the same effect as achieved by the embodiment illustrated in FIG. 5. As will be apparent from FIG. 8, longitudinally opposite ends of the respective crotch region elastic member 70 intersect the adjacent ends of the respective leg elastic members 13 extending on the front and rear sheets 106, 107. Such intersection may be effective also even when the ends of the crotch region elastic member 70 intersect the adjacent end of at least one elastic element in each of the leg elastic members 13. These ends intersecting one another are indirectly bonded together through the intermediary of the center sheet 108, the front sheet 106, the rear sheet 107, hot melt adhesive used to bond these sheets one to another. With such arrangement, a force intending to stretch the leg elastic member 13 is transmitted to the crotch region elastic member 70 and to stretch this elastic member 70 as the diaper 1 is put on the wearer's body. Consequently, if the cover sheet 22 is still in folded state in the vicinity of the notch 8b of the core 21, the elastic member 70 thus stretched causes the cover sheet 22 to restore its state before folded and causes the upper region of the pocket 30 in the vicinity of the crotch region elastic member 70 to be largely opened. The inner side edge 132 of the leak-barrier cuff 25 lies above the inner surface 3a and is deformable in vertical direction as well as in horizontal direction as viewed in FIG. 11. A sleeve-like folded end of the inner side edge 132 wraps a first elastic member 41 extending in the longitudinal direction of the absorbent assembly 3 and attached thereto in stretched state. On the front and rear ends 27, 27 of the absorbent assembly 3, the outer side edge 131 and the inner side edge 132 of the leak-barrier cuff 25 are placed upon each other in a Z- or an inverted Z-shape and bonded together between opposed surfaces of the leak-barrier cuff 25 as well as between the leak-barrier cuff 25 and the cover sheet 22 by means of the adhesive 34, as illustrated by FIG. 13. Opposite ends of the first elastic member 41 are fixed to the front and rear ends 27, 28 of the absorbent assembly 3, respectively, through the intermediary of the leak-barrier cuff 25. In addition to the first elastic member 41, the leak-barrier cuff 25 may be provided in its transversely intermediate region defined between the outer side edge 131 and the inner side edge 132 with a second elastic members 42 attached thereto in longitudinally stretched state so as to extend in the longitudinal direction of the leak-barrier cuff 25 above the inner surface 3a of the absorbent assembly 3. The second elastic member 42 extend in parallel to the first elastic member 41 at least in the crotch region 8 defined between front and rear ends 133, 134 of the leak-barrier cuff 25. As indicated by imaginary lines in FIGS. 11 and 12, the first and second elastic members 41, 42 are stretched and the leak-barrier cuff 25 rises on the inner surface 3a of the absorbent assembly 3 as the diaper 1 is put on the wearer's body.

The sheets 106, 107, 108, 117, 116 and the absorbent assembly 3 placed upon in the order indicated by FIG. 9 and bonded one to another in the order indicated by FIG. 9 may be folded along the center line B—B with the absorbent assembly 3 inside and then transversely opposite side edges of the front sheet 10, the rear sheet 107 and the inner sheet 116 placed upon one another may be bonded together at the spots 4 shown in FIG. 7 to obtain the pants-type disposable diaper 1 illustrated by FIG. 6. Thereupon, the region of the absorbent assembly 3 extending in the crotch region 8 is folded on both sides of the longitudinal center line A—A, as will be seen in FIG. 7. More specifically, the absorbent assembly 3 is folded along the third folding guide line U so that the respective outer surfaces 24 of the core elements 21c, 21e are opposed to each other and the respective outer surfaces 24 of the core elements 21d, 21f are opposed to each other. At the same time, the absorbent assembly 3 is folded along the first folding guide line S and the second folding guide line T so that the inner surface 23 of the core element 21a is opposed to the respective inner surfaces 23 of the core elements 21e, 21d and the inner surface 23 of the core element 21b is opposed to the respective inner surfaces 23 of the core elements 21e, 21f. The leak-barrier cuff 25 becomes slack as the absorbent assembly 3 is folded, so the leak-barrier cuff 25 can be easily folded inward and constitute a part of the folded portion 50. However, the first and second elastic members 41, 42 are stretched and the leak-barrier cuff 25 elastically restores its state before having been folded as the diaper 1 is put on the wearer's body. In other words, the leak-barrier cuff 25 is appropriately resistant to being permanently folded when the absorbent assembly 3 is folded as is the case with the region of the cover sheet 22 extending along the notch 8b of the absorbent assembly 3.

In the state illustrated by FIGS. 6 and 7, the first elastic member 41 attached to the leak-barrier cuff 25 describes U-shape and extends substantially half around the wearer's leg and upper ends of this U-shape indirectly overlap the leg elastic members 13 attached to the front and rear sheets 106, 107, respectively. These elastic members 13, 41 cooperate one with another to ensure the desired fitness of the diaper 1 fully around the wearer's legs. It is possible to replace the first elastic member 41 in the illustrated embodiment by a plurality of elastic members.

To put the diaper 1 on an infant's or a child's body, his or her mother may put the hands inside the peripheral edge of the waist-hole 9 and guide the legs of the infant or child through the leg-holes 11 as the waist-hole 9 is being broadened. In this course, the side edges 26 of the absorbent assembly 3 as 5 well as the leak-barrier cuffs 25 maintain their folded state in the crotch region 8, so practically do not close the leg-holes 11 of the covering chassis 2 and facilitate the infant's or child's legs to be guided through the leg-holes 11. While the absorbent assembly 3 is folded to form the pocket 30, elastic restoration of the crotch region elastic members 70 extending in the back-and-forth direction attached, preferably in stretched state, to the notches 8b of the absorbent assembly 3 function to maintain the pocket 30 defined by the notches 8b sufficiently opened upward to ensure that loose passage can be smoothly and reliably received by the pocket 30.

While the crotch region elastic members 70 have been illustrated and described above to be attached to the cover sheet 22 in the vicinity of the notches 8b of the core 21, it is possible without deviation from the spirit and the scope of the invention to attached the crotch region elastic members 70 to a sheet other than the cover sheet 22 in the vicinity of the notches 8b.

The disposable pull-on wearing article according to the present invention is primarily characterized in that the body fluid absorbent assembly includes the folded portions which define the pocket adapted to be maintained opened upward under elastic restoration of the crotch region elastic members. The pocket largely opened upward in this manner ensures that even viscous body discharges such as loose passage can be smoothly and reliably received by the pocket. The region of the body fluid absorbent assembly containing the core is folded inward and thereby the width of the body fluid absorbent assembly is appropriately reduced. With an advantageous consequence, it is not apprehended that the crotch region might become bulky when the diaper is put on the wearer's body.

What is claimed is:

1. A disposable pull-on wearing article having a front waist region, a rear waist region and a crotch region, said crotch region being provided with a body fluid absorbent assembly extending over said crotch region and further into said front and rear waist regions, said body fluid absorbent assembly having a substantially rectangular shape and having inner surface, outer surface and transversely opposite side edges extending substantially parallel to each other into said front and rear waist regions, said body fluid absorbent assembly being normally curved in a U-shape with said inner surface extending in said front and rear waist regions opposed to itself and, in said crotch region, said body fluid absorbent assembly having a pair of first folding guide lines extending from a midpoint of a crossline extending across said crotch region or from two points on said crossline which are equidistant in opposite directions from said midpoint to said transversely opposite side edges of said body fluid absorbent assembly placed aside toward said front waist region at a crossing angle α with respect to said crossline and a pair of second folding guide lines extending from said midpoint or said two points to said transversely opposite side edges of said body fluid absorbent assembly placed aside toward said rear waist region at a crossing angle β with respect to said crossline, and said body fluid absorbent assembly including a pair of sections of respective transversely opposite side edges defined between said first folding guide line and said second folding guide line to be folded inwardly of said body fluid absorbent assembly along these first and second folding guide lines, said disposable pull-on wearing article further comprising:

said body fluid absorbent assembly comprising a body fluid absorbent core and a body fluid pervious cover sheet adapted to cover said core and to define at least said inner surface of said body fluid absorbent assembly, said core being formed on both sides of said crotch region with notches so as to have a relatively narrow width in said crotch region and a relatively large width in said front and rear waist regions and thereby to have an hourglass-like shape as a whole, said cover sheet having a width substantially in conformity with the sections of said core lying in said front and rear waist regions but having extending outward beyond said notches in said crotch region, and said extensions of said cover sheet beyond said notches or any sheet placed upon said extensions of said cover sheet being provided with crotch region elastic members attached thereto in stretched or non-stretched state so that said crotch region elastic members extend in said back-and-forth direction and intersect said first and second folding guide lines.

2. The pull-on wearing article according to claim 1, wherein said body fluid absorbent assembly is provided along said opposed side edges with leak-barrier cuffs each made of a sheet member, respective said sheet members being folded back in the transverse direction of said body fluid absorbent assembly from said outer surface onto said outer surface so as to cover said opposite side edges and respective outer side edges of said sheet members lying on said outer surface being bonded to said outer surface, longitudinally opposite ends of respective said sheet members lying in said front and rear waist regions being bonded to said outer and inner surfaces, in said notches of said core, respective said sheet members lying on said outer surface being bonded to said cover sheet and said crotch region elastic members being bonded to respective said sheet members.

3. The pull-on wearing article according to claim 1, wherein said crossing angles $\alpha$, $\beta$ are in a range of 10° to 60° and said crossing angle $\beta$ is in a range of 10 to 30°.

4. The pull-on wearing article according to claim 1, wherein said pants-type wearing article is formed with a pair of leg-holes and a leg elastic members attached to upper halves of peripheral portions surrounding the respective leg-holes intersect the adjacent ends of said crotch region elastic members.

* * * * *